(12) United States Patent
Heindl et al.

(10) Patent No.: US 7,563,902 B2
(45) Date of Patent: Jul. 21, 2009

(54) CHEMILUMINESCENT COMPOUNDS AND THEIR USE

(75) Inventors: Dieter Heindl, Paehl (DE); Rupert Herrmann, Weilheim (DE); Wolfgang Jenni, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 660 days.

(21) Appl. No.: 11/339,713

(22) Filed: Jan. 25, 2006

(65) Prior Publication Data

US 2006/0172358 A1 Aug. 3, 2006

Related U.S. Application Data

(63) Continuation of application No. PCT/EP2004/008480, filed on Jul. 29, 2004.

(30) Foreign Application Priority Data

Jul. 30, 2003 (EP) ................... 03016620

(51) Int. Cl.
*C07D 417/04* (2006.01)
*G01N 21/76* (2006.01)
*G01N 33/573* (2006.01)
*C12Q 1/28* (2006.01)

(52) U.S. Cl. .............. 548/159; 548/217; 548/236; 548/204; 548/305.1; 548/311.4; 546/156; 435/7.4; 435/28; 436/172

(58) Field of Classification Search .............. 548/159, 548/217, 236, 204, 305.1, 311.4; 546/156; 514/312, 365, 367, 374, 375, 394, 397; 435/7.4, 435/28; 436/172

See application file for complete search history.

(56) References Cited

U.S. PATENT DOCUMENTS 5,425,978 A 6/1995 Berneth et al.
5,589,328 A 12/1996 Mahant
5,669,819 A 9/1997 Mattingly et al.

FOREIGN PATENT DOCUMENTS

| DE | 3645292 C2 | 2/1988 |
| EP | 0617288 B1 | 9/1994 |
| EP | 1166757 A2 | 1/2002 |
| GB | 914347 | 1/1963 |
| GB | 1001067 | 8/1965 |
| GB | 1569741 | 6/1980 |
| WO | WO 95/19976 | 7/1995 |
| WO | WO 98/56765 | 12/1998 |

OTHER PUBLICATIONS

Adamczyk, M. et al., "Modulation of the Chemiluminescent Signal from N10-(3-Sulfopropyl)-N-Sulfonylacridinium-9-carboxamides," Tetrahedron 55 (1999) 10899-10914.
Aslam, M. et al. Bioconjugation (1998) 216-363, London.
Dodeigne, C. et al., "Chemiluminescence as a diagnostic tool. A review," Talanta 51 (2000) 415-439.
Kessler, C. "Non-radioactive labeling and detection of biomolecules," Springer Verlag, Berlin Heidelberg (1992).
Mayer, A. et al., "Luminescent Labels-More than Just an Alternative to Radioscopes?" Angewandte Chem. Intern. Ed. Engl. 33(1994) 1044-1072.
McCapra, F. et al., "Luminescent Labels for Immunoassay-From Concept to Practice," Journal of Bioluminescence and Chemiluminescence vol. 4, p. 51-58 (1989).
Soundaramani, S. et al., "Boronic Acids for Affinity Chromatography: Spectral Methods for Determinations of Ionization and Diol-Binding Constants," Analytical Biochemistry 178, 125-134 (1989).
Tijssen, "Practice and Theory of Enzyme Immunoassays," (1990) Amsterdam, Elsevier.
Waldrop, A. et al., "Chemiluminescent determination of hydrogen peroxide with 9-acridinecarbonylimidazole and use in measurement of glucose oxidase and alkaline phosphatase activity," Luminescence 2000; 15:169-182.

*Primary Examiner*—Bernard Dentz
(74) *Attorney, Agent, or Firm*—Marilyn Amick

(57) ABSTRACT

The present invention relates to novel chemiluminescent compounds, to a method for synthesizing these compounds, to derivatives and conjugates comprising these compounds, to the use of these compounds or conjugates thereof in chemiluminescence based assays, especially in immunoassays.

21 Claims, 6 Drawing Sheets

$A^-$ = counterion
Z = leaving group

"dark reaction"  "chemiluminescence/ light reaction"

A⁻ = counterion
Z= leaving group

"dark reaction"    " chemiluminescence/ light reaction"

CHEMILUMINESCENT COMPOUNDS AND THEIR USE

RELATED APPLICATIONS

This application is a continuation of PCT/EP2004/008480 filed Jul. 29, 2004 and claims priority to EP 03016620.1 filed Jul. 30, 2003.

FIELD OF THE INVENTION

The present invention relates to novel chemiluminescent compounds, to a method for synthesizing these compounds, to derivatives and conjugates comprising these compounds, to the use of these compounds or conjugates thereof in chemiluminescence based assays, especially in immunoassays.

BACKGROUND OF THE INVENTION

The specific detection and quantification of biological molecules has been accomplished with excellent sensitivity for example by the use of radio-labeled reporter molecules. The first radio immunoassays developed in the end of the 1950's have matured into the most important tools of in vitro diagnostics, especially in medicine, using a broad variety of different detection or reporter systems. Well-known examples of reporter molecules are enzymes, labeled latex beads, fluorescent dyes and especially chemiluminescent dyes.

Reviews describing the theory and practice of specific binding assays are available. The skilled artisan will find all necessary technical details for performing specific binding assays in textbooks like Tijssen, "Practice and theory of enzyme immunoassays" (1990) Amsterdam, Elsevier and various editions of Colowick, S. P., and Caplan, N. O., Methods in Enzymology (1980-1986), Academic Press, dealing with immunological detection methods, especially volumes 70, 73, 74, 84, 92 and 121.

Paralleled by the development of light measuring techniques and the commercial availability of highly sensitive apparatuses, luminophores have in many applications replaced isotopic labels. Some of the new luminescent labels facilitate analyte detection at extremely low levels of sensitivity. Therefore such labels also commercially are very interesting.

Luminescent labels may be subdivided into the group of fluorescent labels and the group of luminescent labels. Whereas fluorescent labels require irradiation of a sample with excitation light in order to detect and measure the fluorescent label present, the luminescent systems, e.g., chemiluminescent systems do not require an extra source of light.

A widely used class of chemiluminescent labels are the acridinium compounds. Their mechanism of chemiluminescence has been extensively studied and is nicely summarized in a review article published by Mayer, A., and Neuenhofer, S., Angewandte Chem. Intern. Ed. Engl. 33 (1994) 1044-1072, Weinheim, VCH Verlagsgesellschaft mbH, as well as in a review article by Dodeigne, C., et al., Talanta (2000) 415-438.

Several mechanisms leading to emission of light according to the chemiluminescence principles have been proposed. Short-lived intermediates are considered part of the processes leading to decarboxylation and emission of light. The processes postulated for acridinium ester labels, resulting in emission of light or in the unwanted side reaction (dark reaction) leading to hydrolysis of the ester, are schematically shown in FIG. 1.

According to the proposed mechanism the carbonyl group (which has been part of the amide or ester bond) by attack of $H_2O_2$ becomes part of a dioxetanone moiety. Spontaneous decomposition of the dioxetanone moiety is accompanied by light emission and yields a heterocyclic ketone and $CO_2$ in case of a carbonyl group, or in more general chemical terms a heterocumulene in case functional equivalents of the carbonyl group had been present.

It is instantly evident from FIG. 1, that the light reaction (LR) and the dark processes (DP) both are dependent on the properties of the leaving group Z.

An essential feature of the acridinium esters used in diagnostic applications is that the ester function has been substituted to carry a suitable leaving group Z. Suitable leaving groups are designed to match as good as possible two essential requirements: stability and high quantum yield.

On the one hand the leaving group of an acridinium esters must be as active as possible, i.e., leaving quite readily under measurement conditions, to allow for a sensitive detection and high quantum yield. This high activity on the other hand, however, goes to the expense of instability towards hydrolysis. Such instabilities are even more critical if such chemiluminescent labels are used for conjugation to biomolecules. The goal to achieve a high chemiluminescence yield and in addition a high stability of the labeled reagent equals to a fine balance act always ending in a compromise between light yield and stability.

To at least partially reduce the problems encountered, new and different leaving groups have been designed and proposed.

EP 617 288 gives examples of appropriate leaving groups. Most popular are N-sulfonamides, e.g., described in U.S. Pat. No. 5,669,819, thioesters as described in DE 3 645 292, hydroxamic acid esters described in WO 98/56765, imidazolides as described by Waldrop III, A. A., et al., Luminescence 15 (2000) 169-182, and pyridinium amides (WO 95/19976).

Besides the acridinium labels, other well known chemiluminescence based systems make use of labels comprising amongst others the following categories, the combination of luciferins with corresponding luciferases, cyclic arylhydrazides, acridinium derivatives, stable dioxetanes, and oxalic acid derivatives.

However, overall only a rather limited number of chemiluminescent basic compounds is known and even less have proven useful for routine diagnostic applications.

It was the task of the present invention to find and identify a novel class of compounds appropriate for chemiluminescence assays which compounds provide for a stable chemiluminescent dye or label on the one hand and for sensitive detection or high quantum yield on the other hand. Such compounds additionally should be suitable for labeling of, or conjugation to a biomolecule, e.g., a specific binding partner. I.e., it should be possible to introduce a coupling group without impairing the chemiluminescence properties of such compounds and/or the compound itself should not interfere with the biomolecule.

It has been found that the compounds of Formula I are chemiluminescent. Since the compounds according to the present invention encompass both storage stability, as well as sensitive detection in chemiluminescent procedures they are also used to label biomolecules and the resulting conjugates with great advantage can be applied in appropriate specific binding assays for detection of an analyte in a sample.

SUMMARY OF THE INVENTION

The present invention relates to novel chemiluminescent compounds of general Formula I:

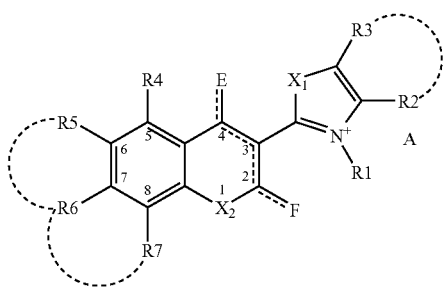

wherein:
one of E or F represents oxygen which is linked to the ring system by a double bond, and one of F or E represents the group:

such that if E represents oxygen, positions 2 and 3 of the ring system are linked by a double bond and, if F represents oxygen, positions 3 and 4 of the ring system are linked by a double bond;

$X_1$ and $X_2$ independently represent —O—, —S—, —NH— or —NR—;

$R^1$ represents alkyl, alkenyl, alkynyl or aralkyl wherein said alkyl, alkenyl or alkynyl can contain up to 20 heteroatoms, and may also contain a coupling moiety;

$R^2$ and $R^3$ can form part of a fused aryl ring; or alternatively $R^2$ and $R^3$ independently represent hydrogen, R, halogen, —$NR_2$, —OR, —OH, —$S(O)_2OH$, —CN, —SCN, —SSR, —SR, —C(O)R, —C(O)H, —C(O)OR, —C(O)OH, —NHC(O)R, —C(O)NHR, —C(O)$NH_2$, —$S(O)_2NHR$ or —$S(O)_2NH_2$;

$R^4$ represents hydrogen, R, halogen, —$NR_2$, —OR, —OH, —$S(O)_2OH$, —CN, —SCN, —SSR, —SR, —C(O)R, —C(O)H, —C(O)OR, —C(O)OH, —NHC(O)R, —C(O)NHR, —C(O)$NH_2$, —$S(O)_2NHR$ or —$S(O)_2NH_2$;

$R^5$ and/or $R^7$ can independently form part of a heteroalkyl ring with $R^8$ or $R^9$, or alternatively $R^5$ and/or $R^7$ are defined as $R^4$ above;

$R^6$ represents —OH, —$OR^8$, —$NH_2$, —$NHR^8$, —$NR^8,R^9$, wherein $R^8$ and/or $R^9$ can form part of a heteroalkyl ring with $R^5$ and/or $R^7$; or $R^8$ and $R^9$ independently represent alkyl, alkenyl, alkynyl or aralkyl wherein said alkyl, alkenyl or alkynyl can contain up to 20 heteroatoms;

R represents alkyl, alkenyl, alkynyl or aralkyl wherein said alkyl, alkenyl or alkynyl can contain up to 20 heteroatoms;

Z represents a leaving group; and

A, if required, represents a counter-ion to balance a net charge of the compound.

The invention also relates to a method for synthesizing the compounds of Formula I, to derivatives and conjugates comprising these compounds, to the use of these compounds or conjugates thereof in chemiluminescence based assays, especially in immunoassays.

DETAILED DESCRIPTION OF THE INVENTION

Figure 1:
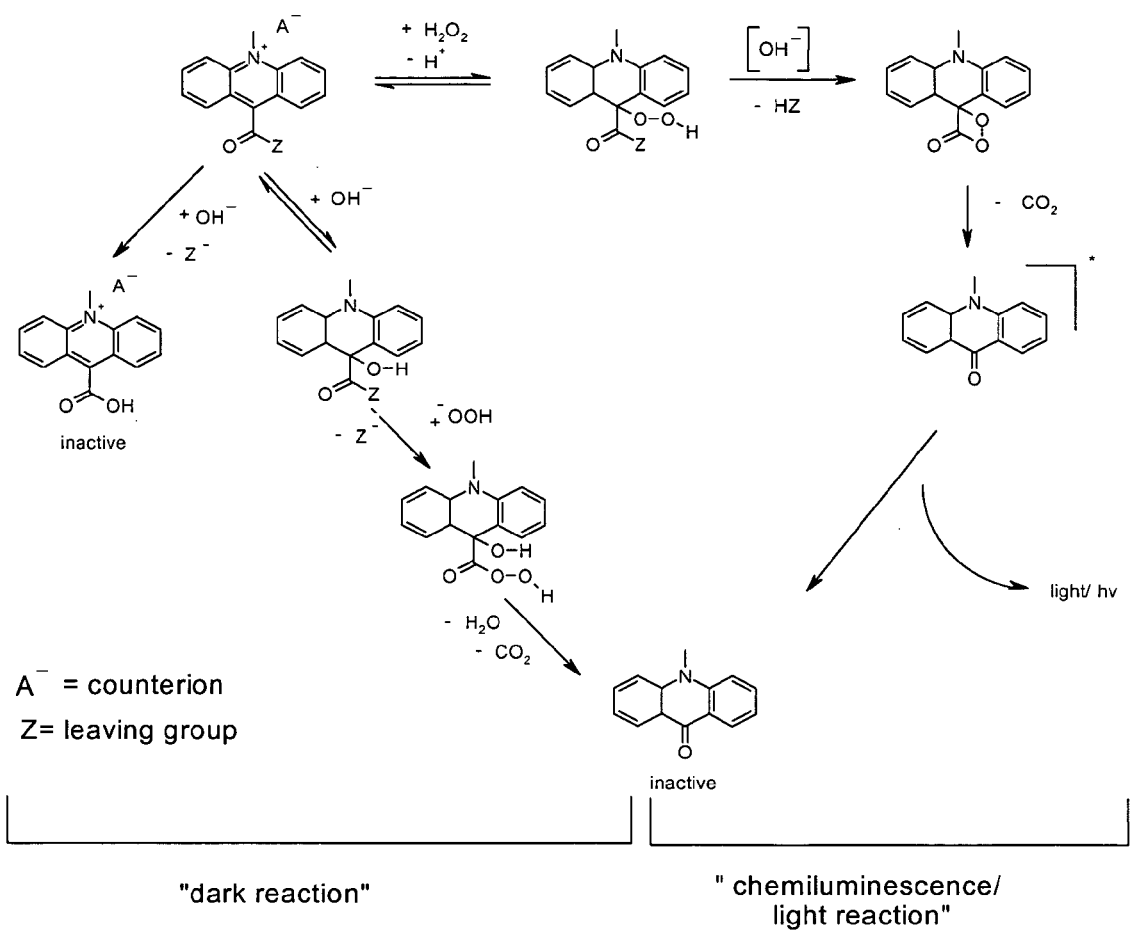
FIG. 1: Acridinium labels. Shown are postulated reaction mechanisms leading to chemiluminescence or non-luminescent decay. Both possible pathways are depicted. The light creating reaction, or light reaction (=LR) leads to chemiluminescence, whereas the dark reaction pathway, or dark process (DP) leads to direct hydrolysis not accompanied by light emission.

In a first embodiment the present invention relates to a compound of Formula I.

The present invention relates to novel chemiluminescent compounds of general Formula I:

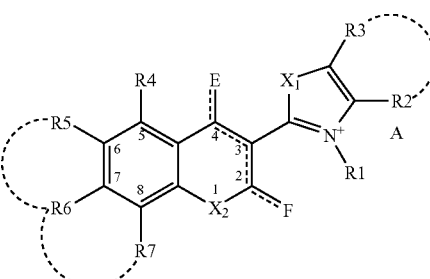

wherein:
one of E or F represents oxygen which is linked to the ring system by a double bond and one of F or E represents the group

such that if E represents oxygen positions 2 and 3 of the ring system are linked by a double bond and, if F represents oxygen positions 3 and 4 of the ring system are linked by a double bond;

$X_1$ and $X_2$ independently represent —O—, —S—, —NH— or —NR—;

$R^1$ represents alkyl, alkenyl, alkynyl or aralkyl wherein said alkyl, alkenyl or alkynyl can contain up to 20 heteroatoms, and may also contain a coupling moiety;

$R^2$ and $R^3$ can form part of a fused aryl ring; or alternatively $R^2$ and $R^3$ independently represent hydrogen, R, halogen, —$NR_2$, —OR, —OH, —$S(O)_2OH$, —CN, —SCN, —SSR, —SR, —C(O)R, —C(O)H, —C(O)OR, —C(O)OH, —NHC(O)R, —C(O)NHR, —C(O)$NH_2$, —$S(O)_2NHR$ or —$S(O)_2NH_2$;

$R^4$ represents hydrogen, R, halogen, —$NR_2$, —OR, —OH, —$S(O)_2OH$, —CN, —SCN, —SSR, —SR, —C(O)R, —C(O)H, —C(O)OR, —C(O)OH, —NHC(O)R, —C(O)NHR, —C(O)$NH_2$, —$S(O)_2NHR$ or —$S(O)_2NH_2$;

$R^5$ and/or $R^7$ can independently form part of a heteroalkyl ring with $R^8$ or $R^9$, or alternatively $R^5$ and/or $R^7$ are defined as $R^4$ above;

$R^6$ represents —OH, —$OR^8$, —$NH_2$, —$NHR^8$, —$NR^8$, $R^9$, wherein $R^8$ and/or $R^9$ can form part of a heteroalkyl ring with $R^5$ and/or $R^7$; or $R^8$ and $R^9$ independently represent alkyl, alkenyl, alkynyl or aralkyl wherein said alkyl, alkenyl or alkynyl can contain up to 20 heteroatoms;

R represents alkyl, alkenyl, alkynyl or aralkyl wherein said alkyl, alkenyl or alkynyl can contain up to 20 heteroatoms;

Z represents a leaving group; and

A, if required, represents a counter-ion to balance a net charge of the compound.

The group $R^1$ preferably is selected from alkyl, sulfoalkyl or alkylamidoalkyl The group $R^1$ is further on preferably selected from alkyl or sulfoalkyl.

More preferred $R^1$ is selected from methyl, ethyl, sulfopropyl and sulfobutyl.

Optionally $R^1$ also comprises a coupling moiety capable of attaching the compound to a protein, a nucleic acid or a specific binding material. Preferably said coupling moiety is selected from the group consisting of N-succinimidyl-oxycarbonyl, maleinimido, 4,6-dichloro-[1,3,5]triazin-2-amino-, N-benzotriazolyl-oxycarbonyl, N-phtalimidyl-oxycarbonyl, carboxylic acid, alkylcarbonyl-oxycarbonyl, arylcarbonyl-oxycarbonyl, alkoxycarbonyl, aryloxycarbonyl, imidate, imidazolide, p-aminobenzoyl, —C(O)Cl, —C(O)Br, —C(O)I, —$SO_2Cl$, —$SO_2Br$, —$SO_2I$, —$NH_2$, —$N_3$, —N=C=O, —N=C=S, —$N_2^+$, —Cl, —Br or —I.

Further preferred the coupling moiety is selected from the group consisting of N-succinimidyl-oxycarbonyl, N-benzotriazolyl-oxycarbonyl, maleinimido, N-phtalimidyl-oxycarbonyl, aryloxycarbonyl as e.g. p-nitrophenyl-oxycarbonyl or pentafluorophenyl-oxycarbonyl, imidate, p-aminobenzoyl, —C(O)Cl, —C(O)Br, —$SO_2Cl$, —$NH_2$, —$N_3$. More preferred the coupling moiety is a N-succinimidyl-oxycarbonyl group or —$SO_2Cl$. Especially preferred the coupling moiety is a N-succinimidyl-oxycarbonyl.

Preferably $X_1$ and $X_2$ are selected from the group consisting —O—, —S—, —NH— or —NR— wherein R represents methyl or ethyl.

More preferred $X_1$ is sulfur or oxygen.

More preferred $X_2$ is oxygen.

The groups $R^5$ and $R^7$ preferably represent hydrogen, or together with $R^8$ or $R^9$ form a heteroalkyl ring, preferably the —$(CH_2)_3$— part of a 6-membered heteroalkyl ring.

Preferably $R^6$ represents —OH, —$NEt_2$, —$NMe_2$ or $NR^8R^9$, wherein both $R^8$ and $R^9$ form together with $R^5$ and $R^7$ a heteroalkyl ring, preferably the —$(CH_2)_3$— part of a 6-membered heteroalkyl ring.

The net charge of a compound according to Formula I obviously will depend on the sum of all charges present. In case the residues $R^1$ to $R^9$ do not contribute to the net charge of the compound of Formula I, it will comprise a single positive net charge due to its oxidized nitrogen. The counter-ion A required will then comprise a single negative charge (=A⁻). The counter-ion A⁻ preferably represents halide, $CH_3SO_4^-$, $CF_3SO_3^-$, $FSO_3^-$, $C_4F_9SO_3^-$, or $CH_3C_6H_4SO_3^-$.

In case the residues $R^1$ to $R^9$ do contribute to the net charge of the compound of Formula I and A represents an cation, it is preferably selected from the group consisting of $K^+$, $Na^+$, tetraalkylammonium.

The leaving group Z is selected from —O—V, —S—V, —N(V)—$SO_2$—V', —O—N(V)—$SO_2$—V', —S—N(V)—V', —O—N(V)—C(O)—V', —O—N=C(V)—V' or —O—N=C(V)—Cl, wherein V or V' independently represent alkyl, which is optionally substituted 1 or 2 times by —$S(O)_2OH$ or 1 to 5 times by fluorine or chlorine, preferably fluorine; and/or V or V' independently represent an aryl moiety corresponding to the following formula

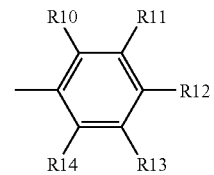

wherein $R^{10}$ and $R^{14}$ independently represent hydrogen, halogen, alkyl, alkenyl, alkynyl, alkoxy, alkylsulfanyl or alkylamido, $R^{11}$ and $R^{13}$ are defined as above $R^2$ and $R^3$, which are not part of a fused aryl ring, $R^{12}$ represents —$R^{15}$—$R^{16}$, wherein $R^{15}$, if present, represents alkyl, alkenyl, alkynyl or alkylamido wherein said alkyl, alkenyl or alkynyl can contain up to 20 heteroatoms, or $R^{15}$, if present, represents an electron-withdrawing group, and $R^{16}$, if present, represents a coupling moiety which is defined as above the coupling moiety optionally comprised in $R^1$. As the skilled artisan will appreciate, such a coupling moiety is present only once in either $R^5$ or $R^{12}$ $R^{11}$ and $R^{12}$, and $R^{13}$ and $R^{12}$ are interchangeable.

The electron-withdrawing group present in $R^{13}$ preferably is selected from —$NO_2$, —CN, —Cl or —$N^+(CH_3)_3$, alkylcarbonyl or alkoxycarbonyl, wherein the alkyl or the alkoxy part is optionally substituted once by aryl.

Preferably Z represents —O—V, —S—V or —NV—$SO_2$—V' and especially preferred Z represents —O—V or —NV—$SO_2$—V'.

The pKa-value of the leaving group Z is among other aspects essential for the chemiluminescence quantum yield on the one hand and for the stability against hydrolysis on the other hand (McCapra, F., et al., J. Biolumin. Chemilumin. 4 (1989) 51-58; Adamczyk, M., et al., Tetrahedron 55 (1999) 10899-10914). To meet these requirements, the pKa-value of the leaving group Z is preferably between 5.0 and 12.5. The corresponding pKa-value can be determined by the method of Soundararajan, S., et al., Analytical Biochemistry 178 (1989) 125-134. More preferred the leaving group Z has a pKa-value between 6.0 and 12.0.

The term "wherein said alkyl, alkenyl or alkynyl can contain up to 20 heteroatoms" refers to the corresponding foresaid alkyl, alkenyl or alkynyl groups. It means that said alkyl, alkenyl or alkynyl groups are optionally interrupted one to five times by —O—, —N(CH$_3$)—, —S—, —S(O)$_2$—, —S(O)$_2$O—, —OS(O)$_2$—, —S(O)$_2$NH—, —NHS(O)$_2$—, —C(O)—, —OC(O), —C(O)O—, —NHC(O)— or —C(O)NH—, and said alkyl, alkenyl or alkynyl groups are optionally substituted one to five times with —S(O)$_2$OH, —OH, —C(O)OH, fluorine or chlorine such that not more than 20 heteroatoms, preferably not more than 15 heteroatoms, also preferably not more than 10 heteroatoms, are comprised in said alkyl, alkenyl or alkynyl groups. Preferably said alkyl, alkenyl or alkynyl groups are optionally interrupted by —O—, —NHC(O)— or —C(O)NH—, and said aliphatic hydrocarbon groups are optionally substituted by —S(O)$_2$OH, —OH, —C(O)OH.

The term "alkyl" denotes a straight-chain or branched saturated hydrocarbon group having 1 to 20, preferably 1 to 10, more preferred 1 to 5 carbon atoms. Examples of the "alkyl groups" include C1-20 alkyl groups, more preferred C1-10 alkyl groups such as methyl, ethyl, propyl, isopropyl, butyl, isobutyl, sec.-butyl, tert.-butyl, pentyl, isopentyl, neopentyl, tert.-pentyl, hexyl, isohexyl, heptyl, octyl, nonyl, decyl, 1,1-dimethylbutyl, 2,2-dimethylbutyl, 3,3-dimethylbutyl and 2-ethylbutyl.

The term "alkenyl" denotes an unsaturated straight-chain or branched aliphatic hydrocarbon group containing one double bond and having 2 to 20, preferably 2 to 10, more preferred 1 to 5 carbon atoms. Examples of the "alkenyl group" include C2-20 alkenyl groups, more preferred C2-10 alkenyl groups such as vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" denotes an unsaturated straight-chain or branched aliphatic hydrocarbon group containing one triple bond and having 2 to 20, preferably 2 to 10, more preferred 1 to 5 carbon atoms. Examples of the "alkynyl group" include C2-20 alkynyl groups, more preferred C2-10 alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "alkoxy" as used herein means an alkyl group as defined above, which is attached via an oxygen-atom.

The term "alkylsulfanyl" as used herein means an alkyl group as defined above, which is attached via an sulfur-atom.

The term "alkylamido" as used herein means an alkyl group as defined above, which is attached via —C(O)NH— or —NHC(O)—.

The term "sulfoalkyl" as used herein means an alkyl group as defined above, which is substituted by —SO$_3$H.

The term "alkylamidoalkyl" means an alkyl group as defined above, which is interrupted once by —C(O)NH— or —NHC(O)—

The term "alkylcarbonyl-oxycarbonyl" means an alkyl group as defined above, which is attached via —C(O)OC(O)— and which is optionally substituted one or several times by —NO$_2$, halogen or —N$^+$(CH$_3$)$_3$.

The term "alkoxycarbonyl" means an alkyl group as defined above, which is attached via —OC(O)— and which is optionally substituted one or several times by —NO$_2$, halogen or —N$^+$(CH$_3$)$_3$.

The term "aryl" denotes a monocyclic or a condensed polycyclic aromatic hydrocarbon group, preferably exemplified by C6-14 aryl groups such as phenyl, naphthyl, anthryl, phenanthryl and 9-fluorenone-2-yl, especially monocyclic or condensed bicyclic aromatic hydrocarbon groups such as phenyl, 1-naphthyl and 2-naphthyl. Preferably aryl means a phenyl moiety.

The term "aralkyl" as used herein denotes an aryl group as defined above attached to a straight chain or branched alkylene group having 1 to 15, preferably 1 to 10, more preferred 1 to 5 carbon atoms. Example of such groups are benzyl, 1-phenethyl, 2-phenethyl as well as phenpropyl and phenbutyl together with their isomers.

The term "arylcarbonyl-oxycarbonyl" means an aryl group as defined above, which is attached via —C(O)OC(O)— and which is optionally substituted one or several times by —NO$_2$, —CN, halogen, —C(O)CH$_3$ or —N$^+$(CH$_3$)$_3$.

The term "aryloxycarbonyl" means an aryl group as defined above, which is attached via —OC(O)— and which is optionally substituted one or several times by —NO$_2$, —CN, halogen, —C(O)CH$_3$ or —N$^+$(CH$_3$)$_3$.

The term "halogen" means fluorine, chlorine, bromine and iodine, especially fluorine and chlorine.

The term "imidate" means an alkyl group or an aryl group as defined above, which is attached via —OC(=NH)—.

The compounds according to the present invention represent very attractive labels, e.g., for labeling of biomolecules. The methods used for coupling of labels to biomolecules have significantly matured during the past years and an excellent overview is given in Aslam, M., and Dent, A., Bioconjugation (1998) 216-363, London, and in the chapter "Macromolecule conjugation" in Tijssen, "Practice and theory of enzyme immunoassays" (1990), Elsevier, Amsterdam.

Appropriate coupling chemistries are known from the above cited literature (Aslam, supra). The chemical compound according to the present invention preferably is designed and synthesized to comprise a coupling group or coupling moiety which matches the coupling chemistry appropriate for the biomolecule under investigation.

In a preferred embodiment the chemical compound according to the present invention comprises a coupling moiety within $R^1$ or $R^{12}$. Preferably the coupling moiety is part of $R^{12}$.

The coupling moiety is a reactive group or activated group which is used for chemically coupling of the compound to a biomolecule. As the skilled artisan will appreciate the coupling moiety is selected to match the chemical function on the biomolecule to which coupling shall be performed.

The chemiluminescent compounds of the present invention, depending on which coupling moiety is selected, can be reacted directly with the biomolecule either in an aqueous or an organic medium.

The chemiluminescent labels can be either directly attached to the biomolecule or connected to the biomolecule via a spacer to form a chemiluminescent conjugate comprising the biomolecule and a compound of the present invention.

Amino groups of biomolecules (the terminal —$NH_2$ group or the $NH_2$ group of a lysine side chain, as well as ω-amino groups of diamino carboxylic acids) can be used for chemical coupling of a marker group thereto based on "amino chemistry". Well-known examples of amino chemistry comprise amongst others the reaction of amino groups with so-called activated groups, like NHS-esters, other activated esters, acid chlorides and azides.

Carboxyl groups on biomolecules (the terminal $COO^-$-group, the carboxy functions of glutamic acid or aspartic acid) are used for chemical coupling based on "carboxy chemistry". Well-known examples of carboxy chemistry comprise amongst others the activation of these carboxy groups to carry the above mentioned activated groups. Coupling to e.g., amino groups on the marker is then easily performed.

Alternatively sulfhydryl groups on biomolecules (e.g. free-SH-groups of cysteine or —SH groups obtained by reducing di-sulfhydryl bridges) are used for chemical coupling based on "sulfhydryl chemistry". Well-known examples of sulfhydryl chemistry comprise amongst others the reaction of —SH groups with maleimido groups, or alkylation with α-halogen carboxylic group or by thioethers.

The hydroxyl group of tyrosine residues or the imidazole group of histidine also may be used to covalent link compounds according to the present invention to a biomolecule by aid, e.g., of diazonium groups.

The coupling moiety may be either part of the chemiluminescent heterocycle of Formula I or of the leaving group. It is generally accepted that large biomolecules may interfere with the luminescent light emitted by the chemiluminescent group if both the chemiluminescent group and biomolecule are in close proximity. It is therefore preferred that the coupling group is part of the leaving group and to preferably use such compound for coupling to a biomolecule. In the case such a conjugate is used in a chemiluminescence assay upon release of the chemiluminescent heterocycle from the biomolecule to which the leaving group remains attached, both molecules the luminophore and the biomolecule no longer are in close proximity. This is advantageous in an assay for detection of an analyte in a sample.

The term "biomolecule" comprises molecules and substances of interest in a therapeutic or a diagnostic field. Biomolecule in the sense of the present invention is any naturally occurring or synthetically produced molecule composed of amino acids, nucleotides, nucleosides, lipids, hormones and/or sugars. As the skilled artisan will appreciate non-naturally occurring derivatives e.g., of amino acids, or nucleotides, like artificial amino acids or artificial nucleotides or nucleic acid analogs may also be comprised in a biomolecule without departing from the spirit of this invention.

In a preferred embodiment the biomolecule is selected from the group consisting of polypeptides, nucleic acids, and low molecular weight drugs. Wherein low molecular weight is a molecular weight below 5000 Da.

Especially preferred are biomolecules which function as a specific binding partner for a biological, biochemical or chemical species.

A conjugate between a biomolecule and a chemiluminescent compound according to the present invention, represents a further preferred embodiment. It will be readily appreciated by the skilled artisan that conjugates between a biomolecule and the chemical compounds described in the present invention are of great advantage, e.g., in a specific binding assay for detection of an analyte in a sample.

It is especially preferred to use a compound according to the present invention or a biomolecule-conjugate comprising such compound in an assay employing chemiluminescence detection. Preferably such chemiluminescence based assay is a specific binding assay, e.g. an immuno assay.

Specific binding assays in general are based on the specific interaction of two members of a bioaffinity binding pair. Examples of preferred specific binding partners in such binding pairs are hapten or antigen and an antibody reactive thereto, biotin or biotin-analogs such as aminobiotin, iminobiotin, or desthiobiotin which binds to biotin or streptavidin, sugar and lectin nucleic acid or nucleic acid analogs and complementary nucleic acid, receptor and ligand for example steroid hormone receptor and steroid hormone, and enzymes and their substrates.

The specific interaction between nucleic acids (or nucleic acid analogs) and nucleic acids complementary thereto in assays based on detection of hybridization between nucleic acid stands and the specific interaction of antibodies with their respective antigen on which the broad range of immunoassays is based, are most relevant in diagnostic routine.

The theory and practice of nucleic acids hybridization assays is summarized in relevant text books, like Kessler, C., "Non-radioactive labeling and detection of biomolecules", Springer Verlag, Berlin Heidelberg (1992). The skilled artisan will find all relevant details therein.

Immunoassays nowadays are broadly used and general knowledge to the skilled artisan. Relevant methods and procedures are summarized in related text books, like Aslam, M., and Dent, A., Bioconjugation (1998) 216-363, London, and Tijssen, "Practice and theory of enzyme immunoassays" (1990), Amsterdam, Elsevier. A comprehensive review can also be found in an article authored by Mayer, A., and Neuenhofer, S., Angewandte Chem. Intern. Ed. Engl. (1994) 1063-1068, Weinheim, VCH Verlagsgesellschaft mbH.

In a further preferred embodiment the present invention relates to a method of performing a chemiluminescence assay based on the use of a compound according to the present invention. Such chemiluminescence based assay method is characterized in that in the presence of trigger solution luminescent light is emitted and can be measured.

Figure 2:
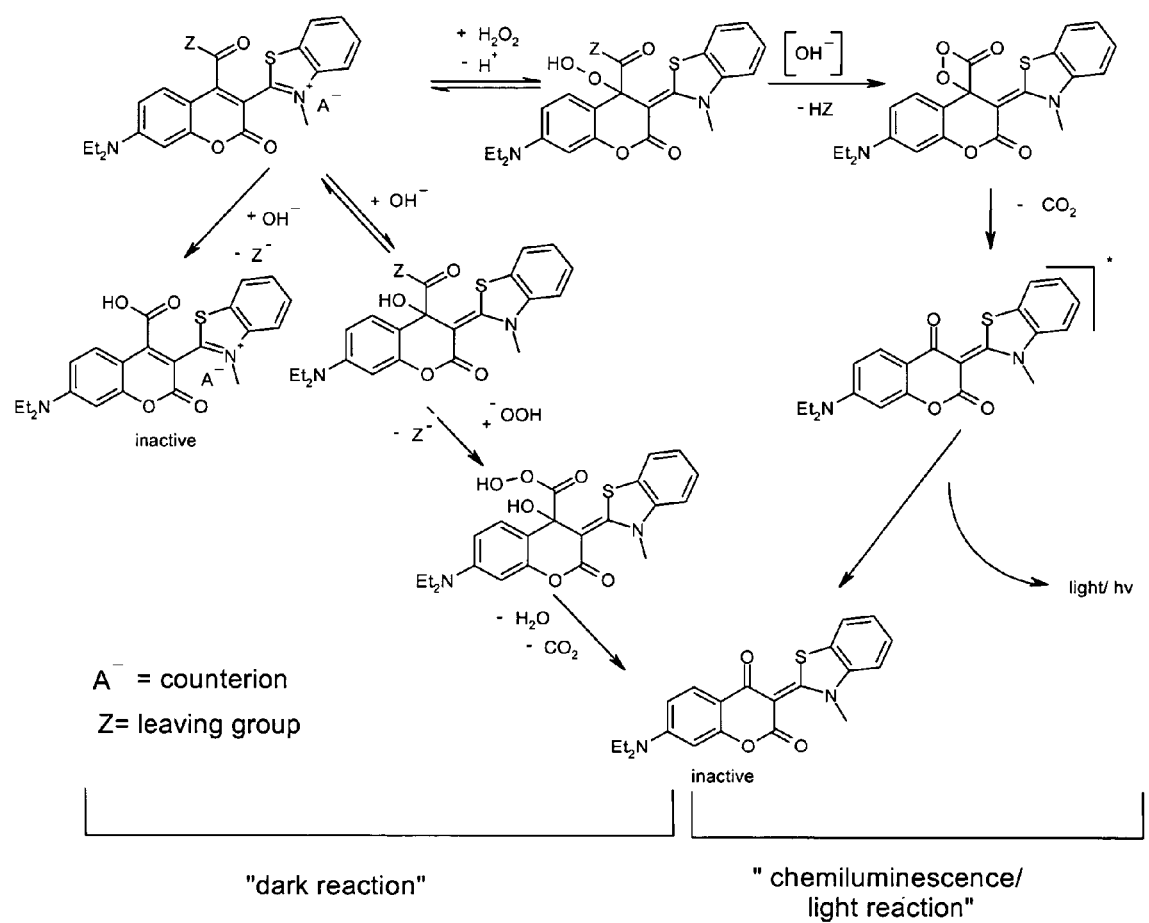
FIG. 2: Mechanism of chemiluminescence for a compound according to Formula I. This schematic represents the likely mechanisms on which chemiluminescence of a compound according to formula I can be based.

Upon the action of a trigger solution, e.g., peroxide or a reactive oxygen species like the oxygen radical anion the chemiluminescent compound of the present invention most likely according to the mechanism illustrated in FIG. 2 forms a dioxetane intermediate which is decarboxylated to generate an electronically excited emitter. The transition to the ground state of this emitter ensues by emission of a photon (=chemiluminescence). The energy (light) which is thereby emitted is measured according to standard procedures and with routine equipment.

As indicated, $H_2O_2$ or a reactive oxygen species like the oxygen radical anion has to be present to form the intermediate dioxetanone. $H_2O_2$ can be added directly or generated indirectly e.g. by enzymatic reaction (glucose oxidase/glucose). Reactive oxygen species are generated during the chemiluminescent reaction from oxygen or $H_2O_2$. Alternatively, a reactive oxygen species can be generated intentionally e.g. by the oxygen initiated C—C coupling (indoxyl-phosphate, U.S. Pat. No. 5,589,328).

Of course the oxidation conditions, i.e., the trigger solution must be chosen such that no destruction of the light emitting molecule occurs and a maximum of light emission is achieved. Trigger solutions may be set up as a single mixture of trigger reagents or triggering may be based on two separate trigger solutions which if combined trigger chemiluminescence. Trigger solutions in the later case for example are 0.5%

H2O2, 0.1 M HNO3 for trigger 1 and 0.25 M NaOH and 0.125% Cetyl trimethyl ammonium chloride (CTAC) for trigger 2.

The generation of the chemiluminescence signal may be accelerated or increased by the use of mediators or enhancers.

Mediators are redox-active compounds facilitating the oxidation of a compound by accelerating electron transfer processes. The mediator is oxidized by the oxidant and oxidizes then the compounds according to the invention, whereby the mediator is reduced again. Typical mediators are hexocyanoferrate (II) and metal complexes like ferrocene. Other enhancers which are used in chemiluminescence reactions include chemicals like iodo-phenol or phenyl boronic acid.

The oxidation preferably is performed in the presence of an appropriate detergent, which creates a hydrophobic microenvironment around the light emitting heterocyclic ketone. This results in an increase of the chemiluminescence quantum yield since quenching due to interaction with water molecules is reduced. Additionally an appropriate fluorophore, like fluorescein can be attached covalent to the detergent or alternatively a fluorophore can be added to the reaction mixture in order to facilitate an energy transfer from the excited emitter, e.g. a heterocyclic ketone to this fluorophore.

The present invention also relates to a method for synthesizing a compound of formula I. Preferably such synthesis comprises the steps of activating the carboxyl moiety on position 2 or 4 of the heterocycle according to Formula II, e.g. by halogenation, or in situ by dicyclohexylcarbodiimide (DCC) or similar reagents.

Formula II:

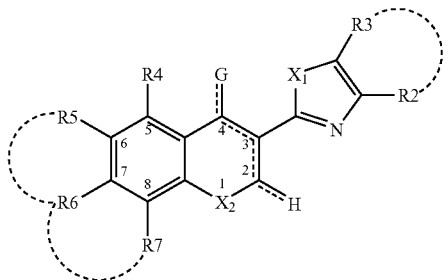

wherein one of G or H represents oxygen which is linked to the ring system by a double bond and one of G or H represents a carboxylic acid group such that if G represents oxygen positions 2 and 3 of the ring system are linked by a double bond and, if H represents oxygen positions 3 and 4 of the ring system are linked by a double bond, and $X_1$, $X_2$ as well as $R^2$ to $R^7$ are as defined above for Formula I.

Then the leaving group Z is introduced in a dry organic solvent eventually supported by adding a non-nucleophilic base, e.g., pyridine, dimethyl aminopyridine (DMAP) and the like. Finally the nitrogen of the heterocyclic ring system at position 1 is alkylated by e.g., methyltriflate, propanesultone or other alkylating reagents.

The examples and figures are provided to aid the understanding of the present invention, the true scope of which is set forth in the appended claims. It is understood that modifications can be made in the procedures set forth without departing from the spirit of the invention.

Specific Embodiments

EXAMPLE 1

Synthesis of 2-oxo-2H-chromene-4-carboxylic Acid Active Ester 5

Synthesis of an oxidative triggerable chemiluminescent coumarin phenolester (phenyl-3-[2-(N-methyl)-benzthiazolium]-7-diethylamino-coumarin-4-carboxylate trifluoromethanesulfonate 4)

Figure 3:
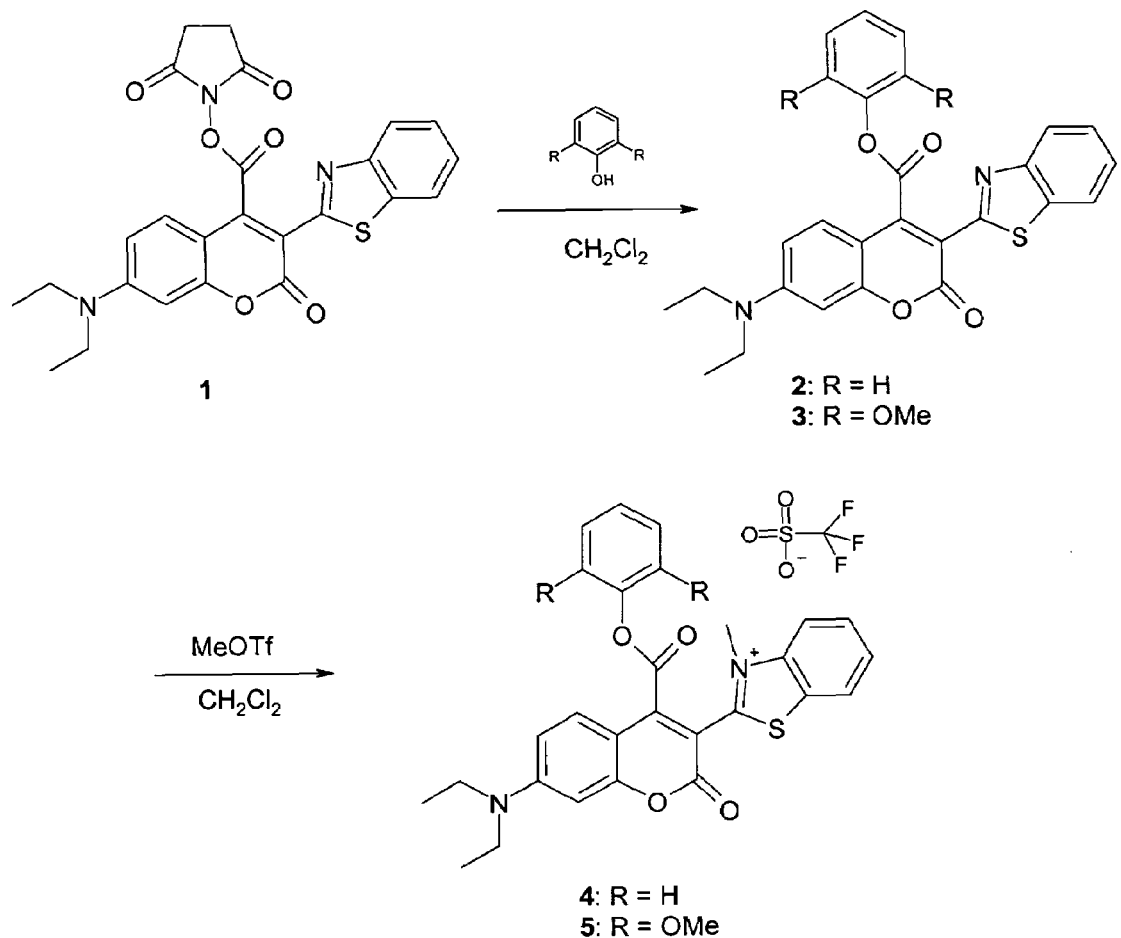
FIG. 3: Synthesis of a 2-oxo-2H-chromene-4-carboxylic acid active ester 5. This schematic represents the synthesis pathway for the oxidative triggerable chemiluminescent Coumarin phenolester Phenyl-3-[2-(N-methyl)-benzthiazolium]-7-diethylamino-coumarin-4-carboxylate trifluoromethanesulfonate 4 according to Example 1.

A schematic representation of this synthesis is given as FIG. 3.

a) Synthesis of phenol 3-(2-benzthiazolyl)-7-diethylamino-coumarin-4-carboxylate 2

To a solution of 20 mg (0.041 mmol) N-succinimidyl-3-(2-Benzthiazolyl)-7-diethylamino-coumarin-4-carboxylate 1 (Fluka, no. 12782) in 2 mL of methylene chloride were added 77 mg (0.82 mmol) Phenol in portions at ambient temperature. The resulting solution was stirred overnight, then diluted in 20 mL of ethyl acetate and washed with saturated solutions of sodium bicarbonate, ammonium chloride and sodium chloride. The organic layer was separated, dried over magnesium sulfate and filtered. Evaporation and drying under vacuum yielded 25 mg of the product 2 as an red-orange solid.

MS: ESI-MS, M+=470.06; Rf=0.78 (Et2O).

b) Synthesis of phenyl-3-[2-(N-methyl)-benzthiazolium]-7-diethylamino-coumarin-4-carboxylate trifluoromethanesulfonate 4:

10 mg of phenyl-3-(2-benzthiazolyl)-7-diethylamino-coumarin-4-carboxylate 2 were dissolved in 0.5 mL methylene chloride and 0.5 mL methyltriflate were added slowly. The solution was stirred subsequently for 60 hours at ambient temperature. Then 5 mL diethylether were added and the resulting precipitate was filtered off, washed two times with 3 mL diethylether and dried under vacuum to afford a red solid. This residue was purified by silica gel column chromatography (Kieselgel 60 from Merck) using chloroform/acetonitrile (0% to 33% acetonitrile) as eluent. The appropriate fractions were collected and pooled. The solvent was removed and 5.5 mg of the product 4 were obtained as red solid.

MS: ESI-MS, M+=485.08; Rf=0.08 (CHCl3/MeCN 4:1); 1H-NMR (CDCl3, 300 MHz): δ(ppm)=1.31 (m, 6H); 3.58 (m, 4H); 4.36 (bs, 3H); 6.75 (m, 1H); 6.92 (m, 1H); 7.11 (m, 2H); 7.37 (m, 2H); 7.53 (m, 2H); 7.99 (m, 3H); 8.22 (m, 1H); 8.36 (m, 1H).

EXAMPLE 2

Synthesis of the Oxidative Triggerable Chemiluminescent Coumarin Phenolester (2,6-dimethoxy)-phenyl-3-[2-(N-methyl)-benzthiazolium]-7-diethylamino-coumarin-4-carboxylate Trifluoromethanesulfonate 5

A schematic illustration of this synthesis is given in FIG. 3.

a) Synthesis of (2,6-dimethoxy)-phenyl-3-(2-benzthiazolyl)-7-diethylamino-coumarin-4-carboxylate 3

To a solution of 20 mg (0.041 mmol) N-succinimidyl-3-(2-benzthiazolyl)-7-diethylamino-coumarin-4-carboxylate 1 (Fluka, no. 12782) in 2 mL of methylene chloride were added 62 mg (0.41 mmol) 2,6-dimethoxy-phenol in portions at ambient temperature. Then the solution was stirred overnight, diluted in 20 mL of ethyl acetate and washed with saturated solutions of 1N NaOH, ammonium chloride and sodium chloride. The organic layer was separated, dried over magnesium sulfate and filtered. Evaporation and drying under vacuum yielded 24 mg of the product 3 as an red-orange oil. The residue was used without further purification in the next reaction step.

Rf=0.74 (Et2O).

b) Synthesis of (2,6-dimethoxy)-phenyl-3-[2-(N-methyl)-benzthiazolium]-7-diethylamino-coumarin-4-carboxylate trifluoromethanesulfonate 5

15 mg of (2,6-dimethoxy)-phenyl-3-(2-benzthiazolyl)-7-diethylamino-coumarin-4-carboxylate 3 were dissolved in 1.0 mL methylene chloride and 0.5 mL methyltriflate were added slowly. The solution was stirred subsequently for 20 hours at ambient temperature. Then 5 mL diethylether were added and the resulting precipitate was filtered, washed two times with 4 mL diethylether and dried under vacuum to afford a red solid. This residue was purified by silica gel column chromatography (silica gel 60 from Merck) using chloroform/acetonitrile (0% to 50% acetonitrile) as eluent. The appropriate fractions were collected and pooled. Evaporation of the solvent yielded 4.5 mg of a red solid.

MS: ESI-MS, M+=545.3; Rf=0.09 (CHCl3/MeCN 4:1).

EXAMPLE 3

Synthesis of an Oxidative Trigerrable Chemiluminescent Coumarin Sulfonylamide Active Ester (N-(4-methoxy-phenyl)-N-(4(tert-butyloxycarbonylethyl)phenyl-sulfonyl)-[2-(N-methyl)-benzthiazolium]-7-diethylamino-coumarin-4-carboxamide trifluoromethanesulfonate 9)

Figure 4:
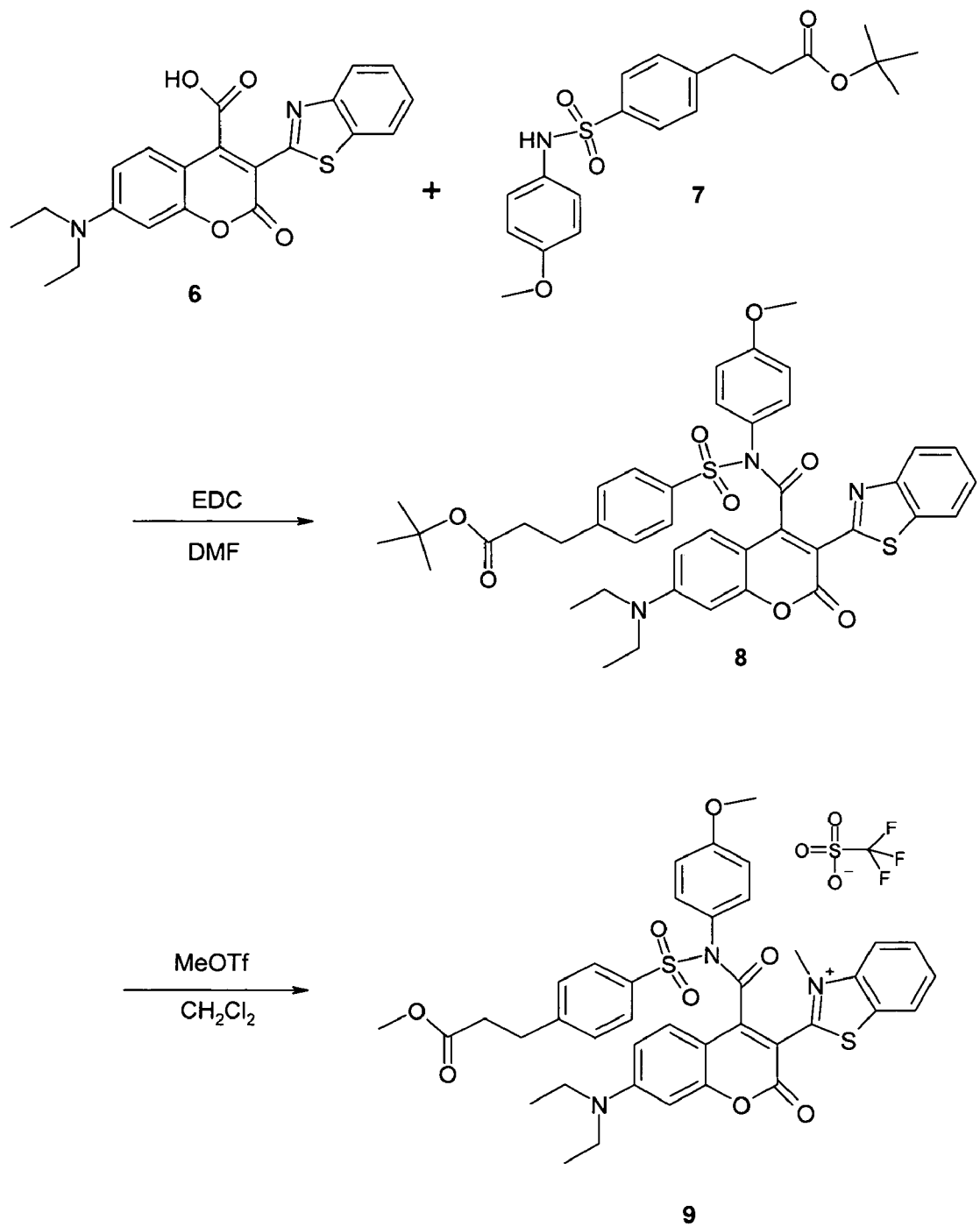
FIG. 4: Synthesis of a an oxidative triggerable chemiluminescent coumarin phenolester. This schematic represents the synthesis pathway for synthesis of (2,6-Dimethoxy)-phenyl-3-[2-(N-methyl)-benzthiazolium]-7-diethylamino-coumarin-4-carboxylate trifluoromethanesulfonate 5 according to example 2.
Figure 5:
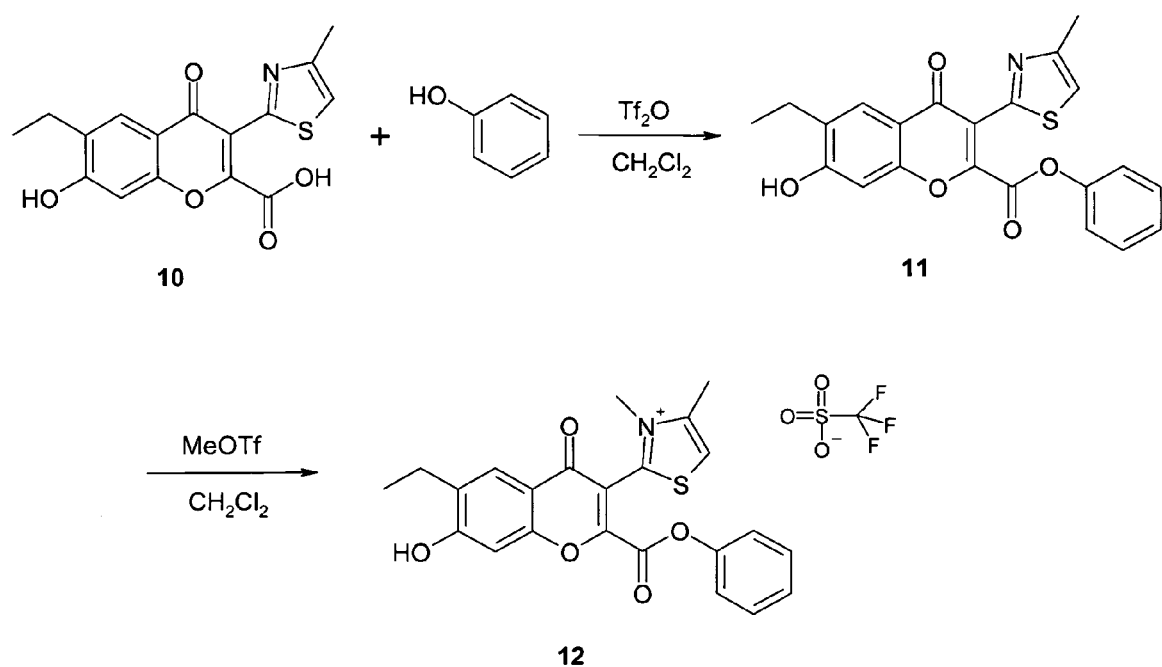
FIG. 5: Synthesis of a coumarin sulfonylamide active ester. This schematic represents the synthesis pathway for the oxidative triggerable chemiluminescent Coumarin sulfonylamide active ester Sulfonyl-3-[2-(N-methyl)-benzthiazolium]-7-diethylamino-coumarin-4-carboxamide trifluoromethanesulfonate 9 according to example 3.

A schematic illustration of this synthesis is given in FIG. 4.

a) Synthesis of tert-butyl-3-[4-(4-methoxy-phenylsulfamoyl)-phenyl)]-propionate 7

A mixture of 6.0 g (24.1 mmol) 3-(4-chlorsulfonylphenyl)-propionic acid, 4 mL tert-butanol, 0.84 mL concentrated sulfuric acid and 4 mL isobutene was placed in an autoclave and stirred for 24 hours at room temperature. Then the reaction mixture was diluted with 250 mL of a saturated sodium bicarbonate solution and extracted three times with 100 mL methylene chloride. The combined organic phases were dried over sodium sulfate, filtered and concentrated under vacuum to give a brownish oil. The crude intermediate was diluted with 140 mL hot hexane, filtered and evaporated to yield a beige solid which was directly dissolved in 50 mL methylene chloride. Then 2.02 g p-anisidine and 250 mg 4-dimethylaminopyridine (DMAP) were added and stirred for 2.5 hours at ambient temperature. After evaporation of the solvent the brown residue was purified by column chromatography on silica gel (eluent: toluene/methanol 4:1). The fractions containing the product were combined, evaporated and dried under vacuum to yield 2.3 g of 7 as a white solid.

MS: ESI-MS, M+=391.01; Rf=0.37 (toluene/methanol 4:1).

c) Synthesis of N-(4-methoxy-phenyl)N-(4(tert-butyloxycarbonylethyl)phenyl-sulfonyl)-3-(2-benzthiazolyl)-7-diethylamino-coumarin-4-carboxamide 8

To a solution of 50 mg (0.127 mmol) 3-(2-benzthiazolyl)-7-diethylamino-coumarin-4-carboxylic acid 6 (Fluka, no. 12781) and 60 mg (0.152 mmol) sulfonamide 7 in 1.5 mL of dimethylformamide were added 36 mg (0.190 mmol) N'-(3-dimethylaminopropyl)-N-ethylcarbodiimid (EDC). After 16 hours at ambient temperature the solution diluted in 20 mL of ethyl acetate and washed with saturated solutions of 1N NaOH, ammonium chloride and sodium chloride. The organic layer was separated, dried over magnesium sulfate and filtered. Evaporation and drying under vacuum yielded 103 mg of a red-orange solid. The residue contained 85% (HPLC-MS, 226 nm) of the product and was used without further purification in the next reaction step.

MS: ESI-MS, M+=767.05; Rf=0.66 (Et2O).

d) Synthesis of N-(4-methoxy-phenyl)N-(4(tert-butyloxycarbonylethyl)phenyl-sulfonyl)-[2-(N-methyl)-benzthiazolium]-7-diethylamino-coumarin-4-carboxamide trifluoromethanesulfonate 9:

20 mg of N-(4-methoxy-phenyl)N-(4(tert-butyloxycarbonylethyl)phenyl-sulfonyl)-3-(2-benzthiazolyl)-7-diethylamino-coumarin-4-carboxamide 8 were dissolved in 0.5 mL methylene chloride and 0.5 mL methyltriflate were added slowly. The solution was stirred subsequently for 16 hours at ambient temperature. Then 5 mL diethylether were added and the resulting precipitate was filtered, washed two times with 3 mL diethylether and dried under vacuum to afford a red solid. The crude product was purified by silica gel column chromatography (silica gel 60 from Merck) using chloroform/acetonitrile (0% to 50% acetonitrile) as eluent. Fractions containing the desired product were collected. Evaporation of the solvent yielded 4.5 mg of a red solid.

MS: ESI-MS, M+=740.2; Rf=0.09 (CHCl3/MeCN 4:1); 1H-NMR (CDCl3, 300 MHz): δ(ppm)=1.32 (m, 6H); 2.73 (m, 2H); 3.07 (m, 2H); 3.57 (m, 4H); 3.70 (s, 3H); 3.86 (s, 3H); 4.04 (bs, 3H); 6.46 (m, 1H); 6.81 (m, 4H); 7.10 (m, 1H); 7.37 (m, 3H); 7.89 (m, 3H); 8.10 (m, 2H); 8.75 (m, 1H).

EXAMPLE 4

Synthesis of an Oxidative Triggerable Chemiluminescent Chromene Phenol Ester (phenyl-3-[2-(3,4-dimethyl)-thiazolium]-6-ethyl-7-hydroxy-4-oxo-4H-chromene-2-carboxylate trifluoromethanesulfonate 12)

a) Synthesis of phenyl-6-ethyl-7-hydroxy-3-[(4-methyl)-1,3-thiazol-2-yl]-4-oxo-4H-chromene-2-carboxylate 11

In a 5 mL Schlenk tube 18 mg (0.054 mmol) 6-ethyl-7-hydroxy-3-[(4-methyl)-1,3-thiazol-2-yl]-4-oxo-4H-chromene-2-carboxylate 10 (Aldrich, no. R66,464-2) were suspended in 0.5 mL methylene chloride. Then 51 mg (0.54 mmol) phenol and 18 μl (0.108 mmol) triflate anhydride were added at ambient temperature. The resulting mixture was stirred for 20 hours, diluted in 10 mL of ethyl acetate and washed with water and saturated solutions of sodium bicarbonate and sodium chloride. The organic layer was separated, dried over magnesium sulfate and filtered. Evaporation of the solvent on a rotavapor yielded 9 mg of a yellow solid. This crude product was used without further purification.

MS: ESI-MS, M+=407.1; Rf=0.2 (petrol ether/ethyl acetate 4:1).

b) Synthesis of phenyl-3-[2-(3,4-dimethyl)-thiazolium]-6-ethyl-7-hydroxy-4-oxo-4H-chromene-2-carboxylate trifluoromethanesulfonate 12:

9 mg (0.022 mmol) of phenol 6-ethyl-7-hydroxy-3-[(4-methyl)-1,3-thiazol-2-yl]-4-oxo-4H-chromene-2-carboxylate 11 were dissolved in 0.5 mL methylene chloride and 14 μl (0.22 mmol) methyltriflate were added to the solution. After stirring for 20 hours at ambient temperature, the reaction mixture was diluted with 3 mL diethylether and the solid was filtered, washed two times with 2 mL diethylether and dried under vacuum to give 7 mg of 11 as a red solid.

MS: ESI-MS, M+=422.1

EXAMPLE 5

Evaluation of phenyl-3-[2-(N-methyl)-benzthiazolium]-7-diethylamino-coumarin-4-carboxylate trifluoromethanesulfonate 4 a) Kinetics

Measurements were performed on a Berthold Lumat LB 953. Two triggers have been used to produce chemiluminescence, both promoting CL-reaction.

Trigger 1: 300 µL; 0.5% H2O2, 0.1 M HNO3
Trigger2: 300 µL; 0.25 M NaOH, 0.125% Cetyl trimethyl ammonium chloride (CTAC)

Coumarin active ester 4 was diluted to 1×10-9 Mol/L in PBS-buffer containing 0.1% Thesit. 100 µL sample was dispensed in a 5 mL Sarsted tube and set into the instrument. Trigger1 was added in position −1, trigger2 in the measuring position. Measurement was performed for 10 sec.

Figure 6:
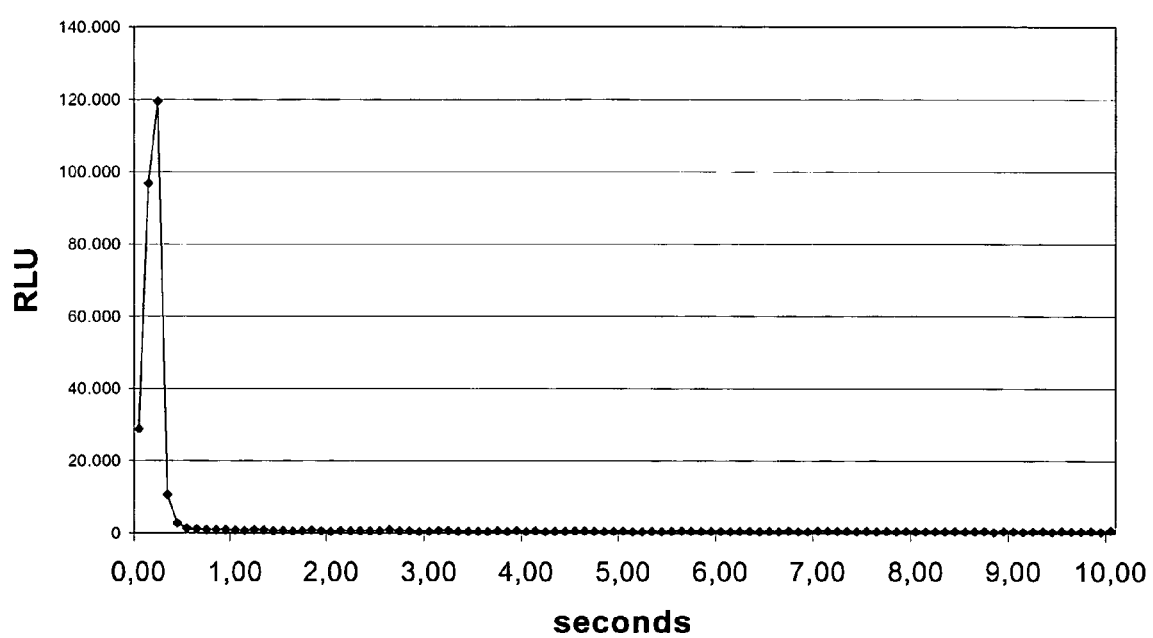
FIG. 6: Chemiluminescence of phenyl-3-[2-(N-methyl)-benzthiazolium]-7-diethylamino-coumarin-4-carboxylate trifluoromethanesulfonate 4. Shown is the chemiluminescence (in relative light units (RLU)) of phenyl-3-[2-(N-methyl)-benzthiazolium]-7-diethylamino-coumarin-4-carboxylate trifluoromethanesulfonate 4. The compound has been used at a concentration of 1×10E-9 mol/l.

The kinetics of light emission for this compound under the above conditions is shown in FIG. 6:

b) Sensitivity

A serial dilution of the coumarin active ester 4 in PBS-buffer containing 0.1% Thesit was performed. Each sample was measured as described above, except for the measuring time which was only 2 sec. The smallest signal still significantly different from the blank was considered as the lower detection limit.

Lower detection limit was found as 1×10-11 Mol/L.

What is claimed is:

1. A compound according to the formula:

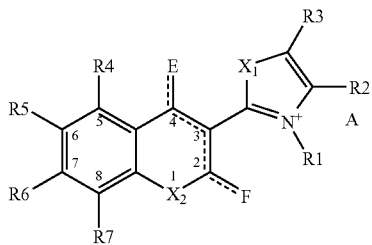

wherein:
one of E or F represents oxygen which is linked to the ring system by a double bond, and one of F or E represents the group

such that if E represents oxygen, positions 2 and 3 of the ring system are linked by a double bond, and if F represents oxygen, positions 3 and 4 of the ring system are linked by a double bond;

$X_1$ and $X_2$ are independently selected from the group consisting of —O—, —S—, —NH—, and —NR—;

$R^1$ is selected from the group consisting of alkyl, alkenyl, alkynyl, aralkyl, and alkyl, alkenyl, alkynyl, aralkyl groups that further comprise a coupling moiety, wherein said alkyl, alkenyl or alkynyl can contain up to 20 heteroatoms;

$R^2$ and $R^3$ are independently selected from the group consisting of hydrogen, R, halogen, —NR$_2$, —OR, —OH, —S(O)$_2$OH, —CN, —SCN, —SSR, —SR, —C(O)R, —C(O)H, —C(O)OR, —C(O)OH, —NHC(O)R, —C(O)NHR, —C(O)NH$_2$, —S(O)$_2$NHR, and —S(O)$_2$NH$_2$, or $R^2$ and $R^3$ together with the atoms to which they are bound form part of a fused aryl ring;

$R^4$ is selected from the group consisting of hydrogen, R, halogen, —NR$_2$, —OR, —OH, —S(O)$_2$OH, —CN, —SCN, —SSR, —SR, —C(O)R, —C(O)H, —C(O)OR, —C(O)OH, —NHC(O)R, —C(O)NHR, —C(O)NH$_2$, —S(O)$_2$NHR and —S(O)$_2$NH$_2$;

$R^5$ and $R^7$ are independently selected from the group consisting of hydrogen, R, halogen, —NR$_2$, —OR, —OH, —S(O)$_2$OH, —CN, —SCN, —SSR, —SR, —C(O)R, —C(O)H, —C(O)OR, —C(O)OH, —NHC(O)R, —C(O)NHR, —C(O)NH$_2$, —S(O)$_2$NHR, and —S(O)$_2$NH$_2$, or $R^5$ and $R^8$, or $R^7$ and $R^9$, or $R^5$ and $R^8$, and $R^7$ and $R^9$ together with the atoms to which they are bound form part of a fused aryl ring;

$R^6$ is selected from the group consisting of —OH, —OR$^8$, —NH$_2$, —NHR$^8$, and —NR$^8$,R$^9$; wherein R$^8$ is selected from the group consisting of alkyl, alkenyl, alkynyl and aralkyl, wherein said alkyl, alkenyl or alkynyl can contain up to 20 heteroatoms, or R$^8$ and R$^5$ together with the atoms to which they are bound form part of a fused aryl ring;

$R^9$ is selected from the group consisting of alkyl, alkenyl, alkynyl, and aralkyl, wherein said alkyl alkenyl or alkynyl can contain up to 20 heteroatoms, or R$^9$ and R$^7$ together with the atoms to which they are bound form part of a fused aryl ring;

R is selected from the group consisting of alkyl, alkenyl, alkynyl, and aralkyl wherein said alkyl, alkenyl, or alkynyl can contain up to 20 heteroatoms;

Z comprises a leaving group; and

A comprises a counter-ion to balance a net charge of the compound.

2. The compound according to claim 1 wherein $X_1$ and $X_2$ are selected from the group the group consisting of —O— and —S—.

3. The compound according to claim 2 wherein $R^1$ is selected from methyl, ethyl, sulfopropyl, and sulfobutyl; and Z further comprises a coupling moiety.

4. The compound according to claim 3 wherein said coupling moiety is selected from the group consisting of N-succinimidyl-oxycarbonyl, maleinimido, 4,6-dichloro-[1,3,5]triazin-2-amino-, N-benzotriazolyl-oxycarbonyl, N-phtalimidyl-oxycarbonyl, carboxylic acid, alkylcarbonyl-oxycarbonyl, arylcarbonyl-oxycarbonyl, alkoxycarbonyl, aryloxycarbonyl, imidate, imidazolide, p-aminobenzoyl, —C(O)Cl, —C(O)Br, —C(O)I, —SO$_2$Cl, —SO$_2$Br, —SO$_2$I, —NH$_2$, —N$_3$, —N=C=O, —N=C=S, —N$_2$+, —Cl, —Br, and —I.

5. The compound according to claim 4 wherein:

$X_1$ is —O— or —S—; and $X_2$ is —O—;

$R^5$ is hydrogen, or $R^5$ and $R^8$ together with the atoms to which they are bound form a heteroalkyl ring;

$R^7$ is hydrogen, or $R^7$ and $R^9$ together with the atoms to which they are bound form a heteroalkyl ring; and $R^6$ is selected from the group consisting of —OH, —NEt$_2$, —NMe$_2$ and NR$^8$R$^9$.

6. The compound according to claim 1 represented by the structure:

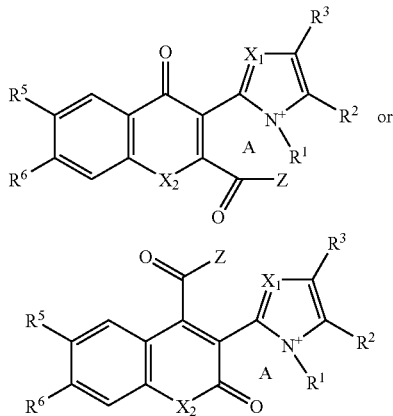

wherein:
- $X_1$ and $X_2$ are independently selected from the group consisting of —O—, —S—, —NH—, and —NR—;
- $R^1$ is selected from the group consisting of alkyl, alkenyl, alkynyl, aralkyl, and alkyl, alkenyl, alkynyl, aralkyl groups that further comprise a coupling moiety, wherein said alkyl, alkenyl or alkynyl can contain up to 20 heteroatoms;
- $R^2$ and $R^3$ are independently selected from the group consisting of hydrogen, R, halogen, —$NR^2$, —OR, —OH, —$S(O)_2OH$, —CN, —SCN, —SSR, —SR, —C(O)R, —C(O)H, —C(O)OR, —C(O)OH, —NHC(O)R, —C(O)NHR, —$C(O)NH_2$, —$S(O)_2NHR$, and —$S(O)_2NH_2$, or $R^2$ and $R^3$ together with the atoms to which they are bound form part of a fused aryl ring;
- $R^5$ is selected from the group consisting of hydrogen, alkyl, alkenyl, alkynyl, and aralkyl wherein said alkyl, alkenyl or alkynyl can contain up to 20 heteroatoms;
- $R^6$ is selected from the group consisting of —OH, —$OR^8$, —$NH_2$, —$NHR^8$, and —$NR^8R^9$; wherein $R^8$ is selected from the group consisting of alkyl, alkenyl, alkynyl, and aralkyl, wherein said alkyl, alkenyl, or alkynyl can contain up to 20 heteroatoms;
- $R^9$ is selected from the group consisting of alkyl, alkenyl, alkynyl, and aralkyl, wherein said alkyl, alkenyl, or alkynyl can contain up to 20 heteroatoms;
- Z comprises a leaving group, and
- A comprises a counter-ion to balance a net charge of the compound.

7. The compound according to claim 6 wherein $X_1$ is —O— or —S—, and $X_2$ is —O—.

8. The compound according to claim 7 wherein Z further comprises a coupling group.

9. The compound according to claim 7 wherein R1 is alkyl; $R^2$ is alkyl, and $R^3$ is hydrogen, or $R^2$ and $R^3$ together with the atoms to which they are bound form part of a fused aryl ring.

10. The compound according to claim 9 wherein $R^5$ is selected from the group consisting of hydrogen and alkyl and R6 is selected from the group consisting of —OH and —$NR^8R^9$; wherein $R^8$ and $R^9$ are independently alkyl.

11. The compound of claim 7 wherein Z is selected from the group consisting of —O—V, —S—V, —N(V)—$SO_2$—V', —O—N(V)—$SO_2$—V', —S—N(V)—V', —O—N(V)—C(O)—V', —O—N=C(V)—V', and —O—N=C(V)—Cl;

wherein V and V' are independently selected from the group consisting of alkyl, substituted alkyl, and an aryl moiety corresponding to the formula:

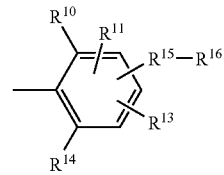

wherein said substituted alkyl is substituted with one or more moieties selected from the group consisting of —$S(O)_2OH$, fluorine, and chlorine;
- $R^{10}$ and $R^{14}$ are independently selected from the group consisting of hydrogen, halogen, alkyl, alkenyl, alkynyl, alkoxy, alkylsulfanyl, and alkylamido;
- $R^{11}$ and $R^{13}$ are independently selected from the group consisting of hydrogen, fluorine, chlorine, —OH, —$C(O)CH_3$, —$S(O)_2OH$, —$S(O)_2NH_2$, and —$S(O)_2NH_2$;
- $R^{15}$ is selected from the group consisting of a bond, an electron-withdrawing group, alkyl, alkenyl, alkynyl, and alkylamido wherein said alkyl, alkenyl, or alkynyl can contain up to 20 heteroatoms; and
- $R^{16}$ is selected from the group consisting of hydrogen and a coupling moiety, with the proviso that the coupling moiety, when present, is only present once in said compound.

12. The compound according to claim 11 wherein:
Z is —O—V— or —N(V)—$SO_2$—V';
V comprises a moiety of the formula:

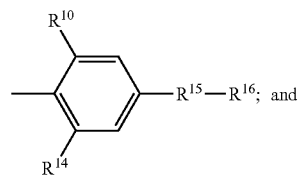

V' comprises a moiety of the formula:

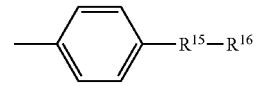

wherein $R^{10}$ and $R^{14}$ are independently selected from the group consisting of hydrogen and alkoxy, $R^{15}$ is selected from the group consisting of a bond, alkyl, alkenyl, alkynyl, and alkoxy, and $R^{16}$ comprises hydrogen or a coupling moiety.

13. The compound according to claim 12 wherein the coupling moiety is selected from the group consisting of N-succinimidyl-oxycarbonyl, N-benzotriazolyl-oxycarbonyl, maleinimido, N-phtalimidyl-oxycarbonyl, p-nitrophenyl-oxycarbonyl, pentafluorophenyl-oxycarbonyl, imidate, p-aminobenzoyl, —C(O)Cl, —C(O)Br, —$SO_2Cl$, —$NH_2$, and —$N_3$.

14. The compound according to claim 13 wherein the coupling moiety is N-succinimidyl-oxycarbonyl or —$SO_2Cl$.

15. A conjugate comprising a compound according to claim 1 and a biomolecule.

16. The conjugate according to claim 15 wherein the biomolecule is a specific binding partner.

17. A conjugate comprising a compound according to claim 11 and a biomolecule.

18. A method of performing a chemiluminescence assay, said assay comprising the steps of providing a compound of claim 1, contacting said compound with $H_2O_2$ or a reactive oxygen species, and measuring luminescence emitted from said compound.

19. The method of claim 18 wherein the $H_2O_2$ or reactive oxygen species is generated by an enzymatic reaction.

20. The method of claim 18 wherein said compound is conjugated to a specific binding partner, said method further comprising the steps of:
    contacting a target analyte with said compound to form complexes comprising the compound and the target analyte;
    separating unbound compounds from said complexes;
    contacting said complexes with $H_2O_2$ or a reactive oxygen species; and
    measuring luminescence emitted from said complexes.

21. A method for synthesizing the compound of claim 1, comprising the steps of:
    activating a carboxyl group at position 2 or 4 of a compound of the formula:

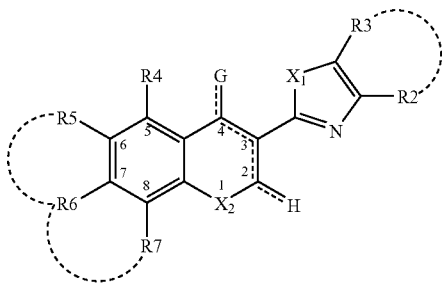

wherein one of G or H represents oxygen which is linked to the ring system by a double bond and one of G or H represents a carboxylic acid group such that if G represents oxygen, positions 2 and 3 of the ring system are linked by a double bond, and if H represents oxygen, positions 3 and 4 of the ring system are linked by a double bond, and $X_1$ and $X_2$ as well as $R^2$ to $R^7$ are as defined as in claim 1;
introducing a leaving group Z; and
alkylating the N-position 1 of the heterocycle.

* * * * *